United States Patent
Kaneko et al.

(10) Patent No.: US 6,171,106 B1
(45) Date of Patent: Jan. 9, 2001

(54) COVER SCREW FOR DENTAL IMPLANT

(75) Inventors: Tadashi Kaneko; Masashi Takahashi, both of Tokyo (JP)

(73) Assignee: GC Corporation, Tokyo (JP)

( * ) Notice: Under 35 U.S.C. 154(b), the term of this patent shall be extended for 0 days.

(21) Appl. No.: 09/392,477

(22) Filed: Sep. 9, 1999

(30) Foreign Application Priority Data

Sep. 14, 1919 (JP) .................................................. 10-259769

(51) Int. Cl.⁷ ........................................................ A61C 8/00
(52) U.S. Cl. ............................................ 433/173; 433/174
(58) Field of Search .................................... 433/172, 173, 433/174, 175, 176, 201.1

(56) References Cited

U.S. PATENT DOCUMENTS

| | | |
|---|---|---|
| 5,569,037 | 10/1996 | Moy et al. . |
| 5,667,384 * | 9/1997 | Sutter et al. ...................... 433/173 X |
| 5,725,377 * | 3/1998 | Lemler et al. ......................... 433/173 |
| 5,769,898 * | 6/1998 | Jisander ........................... 433/173 X |
| 5,810,592 * | 9/1998 | Daftary ................................. 433/173 |
| 5,863,200 | 1/1999 | Hamada et al. . |

\* cited by examiner

*Primary Examiner*—Nicholas D. Lucchesi
(74) *Attorney, Agent, or Firm*—Kanesaka & Takeuchi

(57) ABSTRACT

A cover screw for a dental implant seals a threaded hole of an implant fixture formed in a mandible or maxilla. The cover screw is formed of a main body and a membrane fixing screw, and is attached to the implant fixture until the implant fixture is thoroughly connected to the mandible or maxilla in an implantation hole. The main body includes a first male screw to be screwed into the threaded hole of the implant fixture, an outer face formed on a side opposite to the male screw and facing an oral cavity, and a threaded hole formed on a side of the outer face. The threaded hole has a diameter smaller than that of the male screw and extends parallel to the male screw. The membrane fixing screw has a head, and a second male screw to be screwed in the threaded hole. A barrier membrane is properly held between the main body and the head.

8 Claims, 2 Drawing Sheets

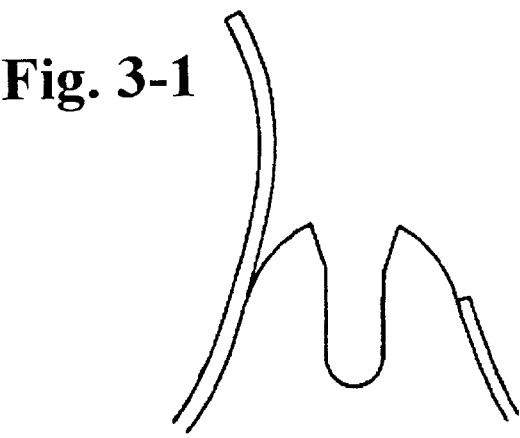
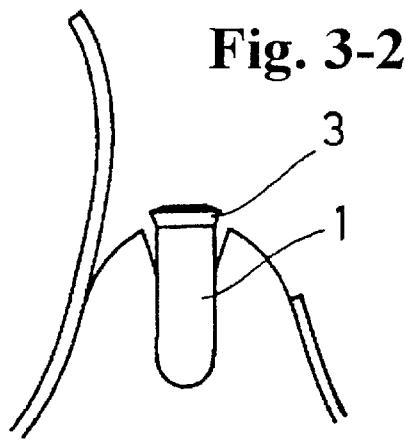
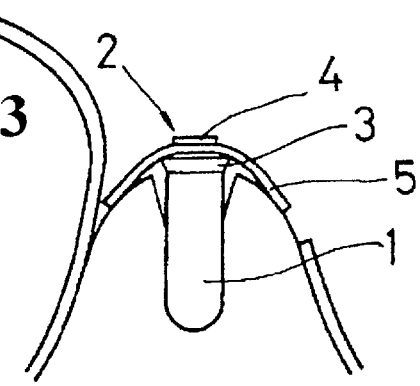
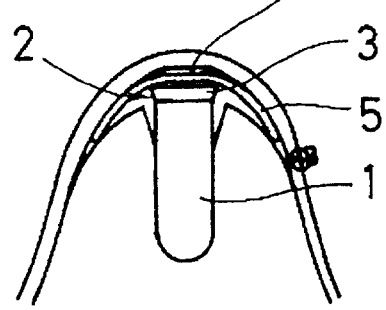
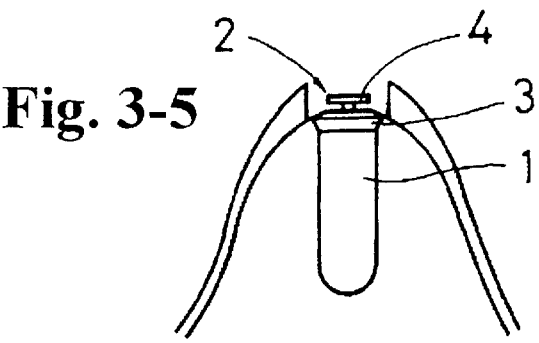
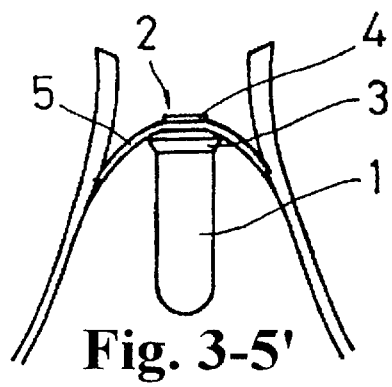
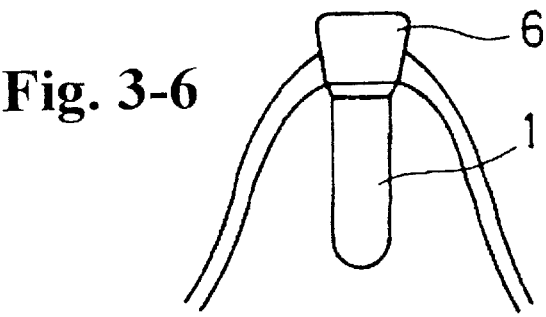

COVER SCREW FOR DENTAL IMPLANT

BACKGROUND OF THE INVENTION AND RELATED ART STATEMENT

The present invention relates to an improvement of a cover screw for a dental implant to seal a threaded hole, which is open on the oral cavity side of an implant fixture implanted in an implantation hole formed in a mandible or maxilla (hereinafter sometimes referred to as only "mandible") of the deficit tooth portion, until the implanted implant fixture is thoroughly connected to the mandible in the implantation hole.

Hitherto, as the dental prosthetic method in a missing tooth portion, a method for using a bridge and a method for using a denture have been generally employed.

However, in the method to use a bridge, since healthy natural teeth on both sides of the missing tooth portion are cut to prepare abutment teeth with which a metallic body provided for a dental prosthesis to be positioned in the missing tooth position is engaged, the method had such defects that not only the healthy natural teeth must be cut to provide engaging portions, but also a bone resorption is likely caused in the missing tooth portion because an occlusion pressure is not directly applied to the dental prosthesis part positioned in the missing tooth portion.

Also, in the method to use a denture, an artificial tooth is fixed to a denture base made of a synthetic resin or the like to prepare a dental prosthesis. According to this method, the occlusal force which is applied to the dental prosthesis is supported by the remaining natural teeth and/or the oral mucosa adjacent to the denture. Therefore, the method involves such defects that a sense of incongruity is generated during the use of the dental prosthesis, and the denture base covers receptors of the taste in the oral mucosa tissue, thereby generating blunting of the taste. In addition, the method has a serious defect that a loss of the residual ridge is caused during the use for a long period of time.

Thus, as a therapeutic method for overcoming these defects, a technology of dental implant has been developed and used, in which an implant fixture acting as a retention of a dental prosthesis or an artificial tooth root is implanted in an implantation hole formed in a mandible of the missing tooth portion to be connected to the mandible to function as a tooth root in a natural tooth, and a fixture for a dental prosthesis is connected and fixed to the abutment fixed to the implant fixture in its oral cavity side, whereby a dental prosthesis is fixed to this fixture for a dental prosthesis.

When a therapeutic method to use such a dental implant is used, the dental prosthesis can be fixed without covering the oral mucosa. Therefore, this method has advantages such that neither a sense of incongruity nor blunting of the taste occurs when the dental prosthesis is installed, and the dental prosthesis is felt like natural teeth. Also, the bone resorption highly expected in the case where no implant fixture is implanted can be suppressed at the minimum because a proper occlusal force is imparted to the mandible. Thus, this therapeutic method has been developed rapidly to such an extent that it can be applied to not only the case where a single tooth is lost, or two or more teeth are lost but also the case of an edentulous jaw (i.e., all teeth are lost).

In the therapeutic method to use such a dental implant, a double technique is mainly employed in which, after an implant fixture implanted in an implantation hole formed in a mandible is thoroughly connected to the mandible of the missing tooth, and the operated portion where the implantation hole has been formed is healed, a gingiva portion at the oral cavity side having the implant fixture implanted therein is again cut to fix an abutment, in which a fixing device of a dental prosthesis is installed, to the oral cavity side of the implant fixture.

In the therapeutic method to use the dental implant according to the double technique, the first operation includes, 1) cutting and opening a gingiva portion at a missing tooth portion in which an implant fixture is implanted, to make a gingival flap, 2) forming an implantation hole for an implant fixture in an exposed alveolar bone of a mandible, 3) implanting the implant fixture within the implantation hole, 4) in order not only to seal a threaded hole which is open on the oral cavity side of the implanted implant fixture but also to prevent a bone of the mandible from growing more inward toward the oral cavity side, screwing a cover screw for a dental implant into the threaded hole which is open on the oral cavity side of the implanted implant fixture, 5) covering the exposed alveolar bone of the mandible with the gingival flap while returning the gingival flap to the original position, and 6) suturing the gingival flap at the cut and opened site. The cover screw has a truncated conical portion with an end portion on the implant fixture side having a size equal to or larger than that of an end portion of the column like portion of the implant fixture and the outer diameter increasing gradually in a direction apart from the implant fixture, and a succeeding truncated cone like portion with the outer diameter decreasing gradually in a direction apart from the implant fixture. The cover screw also includes a concave portion on the face on the implant fixture side, in which a rectangular pipe portion projecting from the end of the implant fixture on the oral cavity side can be inserted, and a screw at the center of the concave portion.

The second operation is carried out after the implant fixture implanted in the implantation hole formed at the mandible of the missing tooth portion is thoroughly connected to the mandible within the implantation hole (usually it takes from 3 to 6 months). The second operation includes, 1) cutting and opening the gingiva portion at the top of the alveolar bone in which the implant fixture is implanted, to form a gingival flap, 2) exposing the cover screw for the dental implant, 3) removing the cover screw for the dental implant, which is screwed in the implant fixture, 4) screwing a screw into the threaded hole of the implant fixture, 5) returning the gingiva petal to the original position and covering the exposed alveolar bone of the mandible with the gingival flap while the healing abutment is exposed, and 6) suturing the gingival flap at the cut and opened site. The screw is formed on the implant fixture side of a healing abutment, and is structured such that an end portion thereof on the implant fixture side has a size approximately equal to that of the end portion of the implant fixture on the oral cavity side, a length thereof is larger than a thickness of the surrounding gingiva, and the shape thereof on the implant fixture side is approximately the same as that of the abutment.

In the second operation, it takes about one month for the cut site to heal. When the gingiva touches the healing abutment on the implant fixture side, the healing abutment is removed. An abutment, a shape thereof on the implant fixture side being approximately identical to that of the healing abutment on the implant fixture side, is disposed at the oral cavity side of the implant fixture. An intermediate bolt is screwed into the threaded hole of the implant fixture while penetrating the abutment to fix the abutment to the implant fixture on the oral cavity side. Then, a gold cylinder having a dental prosthesis on its outside face is disposed on the oral cavity side of this abutment. The dental prosthesis is fixed to the implant fixture on the oral cavity side via the abutment by the intermediate bolt penetrating the gold cylinder or by screwing a gold screw into a threaded hole formed in the abutment, resulting in completing the operation for the dental implant.

When the first operation for the above mentioned dental implant is carried out, the implantation hole for the implant fixture is formed in the alveolar bone of the mandible which is exposed by cutting and opening the gingiva at the missing tooth portion where the implant fixture is implanted. When the implant fixture is implanted in the implantation hole, in case of an insufficient amount of bone in the implantation site of the mandible or of the bone defect, it happens that the implanted implant fixture is exposed to the oral cavity side. If there is a possibility that the undesirable event mentioned above occurs, it is desirable to cover the exposed portion of the implant fixture in order to ensure an area of the bone binding site of the implant fixture and to reduce a risk of a bone resorption caused by a load. Therefore, a bone graft or filling of a bone graft material is often performed before or at the same time of implanting the implant fixture.

However, the bone graft using the bone from a patient oneself increases the burden to the patient, and has a limitation for collecting a sufficient amount of bone. On the other hand, the bone graft using the bone from other person or animal has problems, such as infection and invasion of protein of other person or animal into a body, and the use of the bone graft material has a defect that it can not be replaced by a bone. In addition, there is sometimes a problem that it is hard to graft the bone satisfactorily or to fill the bone graft material into the site to fill.

In order to solve the above mentioned problems, it is ideal that an insufficient bone is supplemented in a body of a patient. Recently, a guided tissue regeneration method using a barrier membrane has been established and used in a dental clinical field. The guided tissue regeneration method provides a space for a regenerated bone under the periosteum of a bone defect portion using the barrier membrane, and induces a bone tissue there by filling blood clot. Therefore, it is important to fix the barrier membrane in order to provide a space.

The conventional method to fix the barrier membrane, used to perform the guided tissue regeneration method, includes;

1. a method in which the barrier membrane is disposed over a cover screw screwed to an implant fixture, and the barrier membrane is fixed to a mandible by driving an absorbable or non-absorbable pin into the mandible.
2. a method in which the barrier membrane with a hole formed by removing a portion corresponding to a cover screw is disposed over a cover screw screwed to an implant fixture, and the barrier membrane is fixed to a mandible by driving an absorbable or non-absorbable pin into the mandible.
3. a method in which the tissue barrier membrane is fixed by disposing it between an implant fixture and a cover screw when the cover screw is screwed to the implant fixture.

However, in the first method, it is very difficult to handle the pin in an oral cavity because the pin is very small. The operation to fix the barrier membrane is complicated because a plurality of pins are used, and the alveolar bone is invaded by the pin used. If the bone grows and touches the face of the cover screw on the oral cavity side, an amount of bone to be cut to detach the cover screw increases in the second operation in which the cover screw is detached and a male screw of a healing abutment is screwed to the threaded hole of the implant fixture, resulting in increasing a load to a patient.

On the other hand, in the second method, in case there is a bone defect portion around the oral cavity side of an implant fixture in an alveolar bone of a mandible in which an implantation hole for an implant fixture is formed in a missing tooth portion, there is a possibility that a portion of the fixed barrier membrane on the implant fixture side sinks in the bone deficit portion. Also, there is a possibility that an undesirable periodontal tissue comes out from a boundary between a portion of the implant fixture on the oral cavity side and the hole of the barrier membrane.

In the third method, in case of using a non-absorbable membrane as the barrier membrane, there is a possibility that the mechanical surface property of the surface of the implant fixture on the oral cavity side becomes worse when the barrier membrane is attached or removed. Therefore, during the second operation, it may happen that the healing abutment can not be fixed closely to the implant fixture, or when the healing abutment is removed and a dental prosthesis is fixed, the abutment can not be fixed closely to the implant fixture. In case of using an absorbable membrane, as the barrier membrane is absorbed, an undesirable periodontal tissue may invade between the surface of the implant fixture on the oral cavity side and the cover screw. When the invasion happens, there is a possibility that during the removal of the periodontal tissue, the mechanical surface property of the surface of the implant fixture on the oral cavity side becomes worse, resulting in such events that during the second operation, the healing abutment can not be fixed closely to the implant fixture, or when the healing abutment is removed and a dental prosthesis is fixed, the abutment can not be fixed closely to the implant fixture. There is, also, a serious defect that the bone tissue may not possibly grow enough to reach the side surface of the cover screw.

The object of the present invention is to solve the defects of the conventional method mentioned above, and to provide a device for securely fixing in an ideal condition a barrier membrane, which provides a space for a regenerated bone under the periosteum by a guided tissue regeneration method using a barrier membrane when an implant fixture implanted in an implantation hole formed in a mandible at the missing tooth portion is connected to the mandible and/or maxilla within the implantation hole.

SUMMARY OF THE INVENTION

During the course of the intensive study to solve the object mentioned above, the present inventors have found that a cover screw for a dental implant to seal a threaded hole, which is open on the oral cavity side of an implant fixture implanted in an implantation hole formed in a mandible and/or maxilla of the missing tooth portion until the implanted implant fixture is thoroughly connected to the mandible and/or maxilla in the implantation hole, is formed of a main body and a membrane fixing screw. The main body has a screw to be screwed in a threaded hole opening on the oral cavity side of the implant fixture, and a threaded hole with a small diameter which is formed on the face of the oral cavity side opposite to the screw side in parallel to the screw. The membrane fixing screw is screwed into the above mentioned threaded hole with the small diameter and has a head for holding a barrier membrane together with the above mentioned face of the oral cavity side of the main body.

It has been found to be preferable that, a center axis of the threaded hole with the small diameter which is formed on the face of the oral cavity side of the main body coincides with that of the screw of the main body which is screwed in the threaded hole opening on the oral cavity side of the implant fixture; the main body and the membrane fixing screw are made of pure titanium or titanium alloy; and a non-skid processing is carried out on the surface of the oral cavity side of the main body. It has also been found that, so as to be able to screw the male screw in the threaded hole with the small diameter of the main body, the membrane fixing screw may have a head either with a connecting portion used for a driver, or with a polygonal shape.

BRIEF DESCRIPTION OF THE DRAWINGS

FIGS. 3-1 to 3-6 are explanatory views showing processes of first and second operations for a dental implant, using the cover screw for the dental implant and the barrier membrane in accordance with the present invention.

DETAILED DESCRIPTION OF A PREFERRED EMBODIMENT

Figure 1:
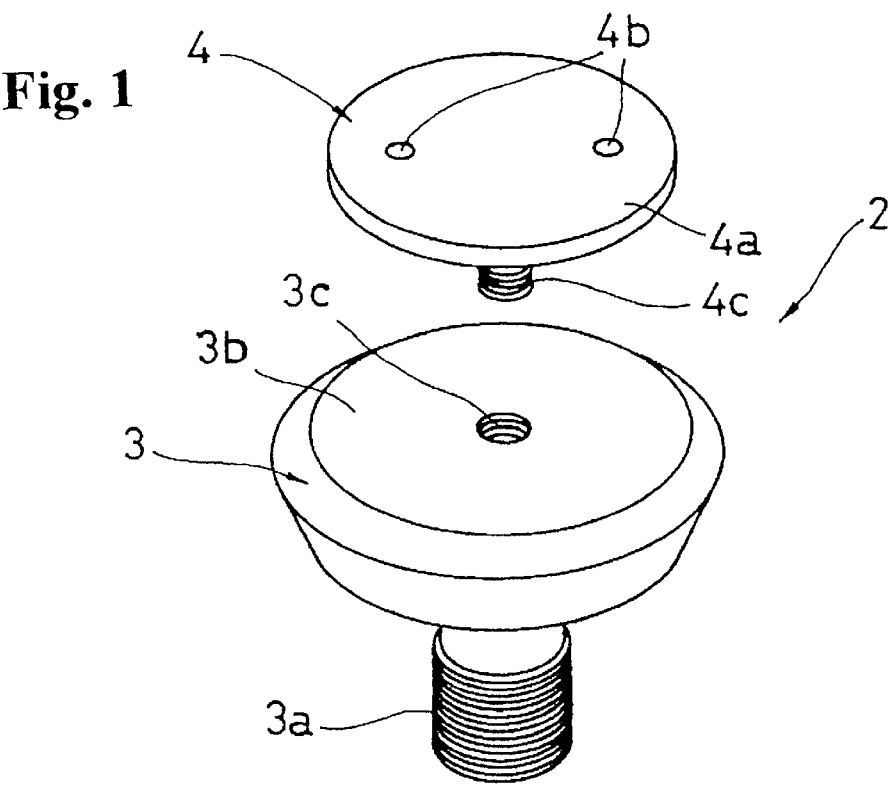
FIG. 1 is a perspective view of a main body and a membrane fixing screw shown in a separated condition in an embodiment of a cover screw for a dental implant in accordance with the present invention.

An embodiment of a cover screw for a dental implant in accordance with the present invention is described in detail with reference to the drawings.

In the drawings, numeral 1 shows an implant fixture in a dental prosthesis maintaining device, which is usually called a dental implant and is fixed by implanting in an implantation hole formed in a mandible of a missing tooth portion. In the embodiment shown here, a front side of the implant fixture implanted in the implantation hole formed in the mandible of the missing tooth portion has an approximate hemisphere shape, and a portion succeeding thereto has an approximate column shape. At an end portion positioned on the oral cavity side of the column like portion, there is provided an angular pipe portion which is connected to an angular pipe concave portion of an abutment almost without slack when the rotation of the abutment disposed on the oral cavity side is prohibited after the wound by the second operation is healed (when a dental prosthesis is used for a single tooth). A threaded hole 1a is formed to extend from a center portion of the angular pipe portion toward the above mentioned approximate column portion.

Numeral 2 shows a cover screw for a dental implant in accordance with the present invention to seal the threaded hole 1a, which is open on the oral cavity side in the implant fixture 1 implanted in the implantation hole formed in the mandible of the missing tooth portion, until the implanted implant fixture 1 is thoroughly connected to the mandible in the implantation hole. The cover screw 2 includes a main body 3, which has a male screw 3a to be screwed into the threaded hole 1a opening to the oral cavity side of the implant fixture 1 and a threaded hole 3c with a small diameter which is formed on the face 3b of the oral cavity side opposite to the screw side parallel to the screw 3a, and a membrane fixing screw 4, which has a head 4a to hold a barrier membrane 5 between the above mentioned face 3b of the oral cavity side of the main body 3 and itself and has a screw 4c to be screwed into the above mentioned threaded hole 3c of the main body 3.

The shape of the main body 3 is similar to that of the conventional cover screw except that the above mentioned threaded hole 3c with the small diameter is formed. An end portion on the implant fixture 1 side has a size equal to or larger than that of the end portion of the approximate column portion of the implant fixture 1. The main body 3 has the truncated conical portion with the outer diameter increasing gradually in a direction apart from the implant fixture 1, and the succeeding truncated cone like portion with the outer diameter decreasing gradually in a direction apart from the implant fixture. Also, the main body 3 includes a concave portion 3d at the side of the implant fixture 1 in which the angular pipe portion projecting from the end of the implant fixture 1 on the oral cavity side can be inserted, and the screw 3a is formed at the center of the concave portion.

It is preferred that the main body 3 is made of titanium or titanium alloy which has a good affinity to a living body.

The face 3b on the oral cavity side of the main body 3 may be flat so as to surely hold the barrier membrane 5 between the head 4a of the membrane fixing screw 4 and the face 3b. It is preferable that a non-skid processing is applied on the face 3b of the main body 3 so as to hold the barrier membrane more surely. It is also preferred that the center axis of the threaded hole 3c with the small diameter formed on the face 3b on the oral cavity side of the main body 3 coincides with that of the screw 3a of the main body 3 screwed in the threaded hole 1a which is open on the oral cavity side of the implant fixture 1, for the purpose that the reduction of the strength of the screw 3a of the main body 3 by forming the threaded hole 3c is prevented.

The head 4a of the membrane fixing screw 4 is to hold the barrier membrane 5 between the face 3b on the oral cavity side of the main body 3 and the head 4a. Therefore, the face on the screw 4c side of the membrane fixing screw 4 is flat, and the head 4a has either a connecting portion 4b for a driver or a polygonal shape so as to be rotated by a wrench, so that the screw 4c can be screwed into the threaded hole 3c with the small diameter of the main body 3. The connecting portion 4b may be a slot, cross shaped hole, polygonal hole, or holes formed in parallel at predetermined intervals so that a pin can be inserted therein.

It is preferred that the membrane fixing screw 4 is made of pure titanium or titanium alloy which has a good affinity to a living body.

The processes of the first operation for a dental implant, using the cover screw for the dental implant including the above mentioned main body 3 and the membrane fixing screw 4 in accordance with the present invention, are described according to FIGS. 3-1 to 3-6.

Process 1: A gingiva portion corresponding to a missing tooth portion in which the implant fixture 1 is implanted is cut and opened at its lip or cheek side from the top of the alveolus to make a gingival flap, and an implantation hole for the implant fixture 1 is formed in an exposed alveolar bone of a mandible (FIG. 3-1).

Figure 2:
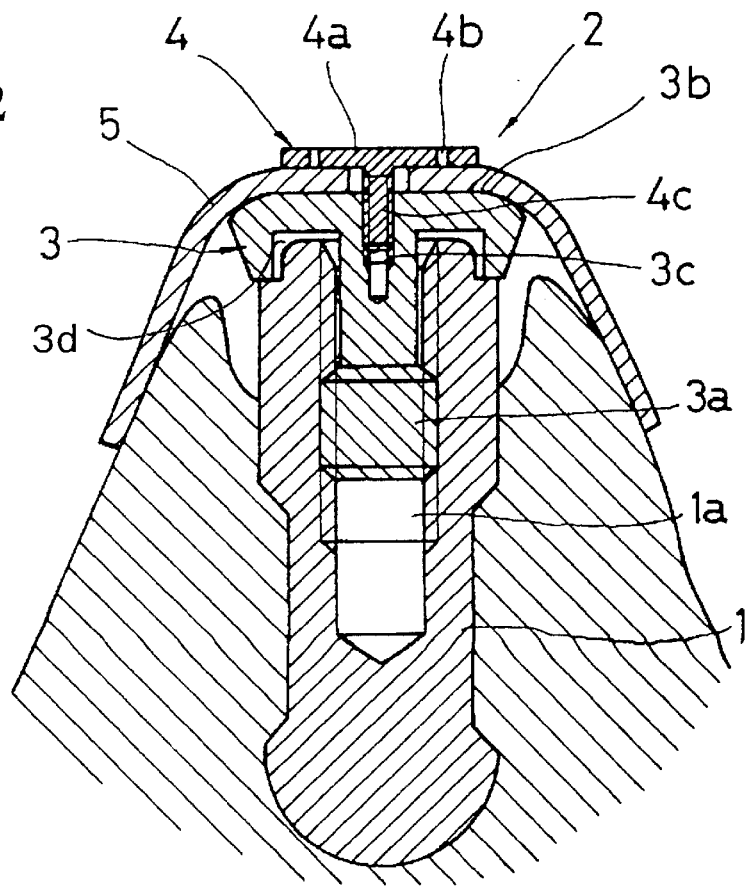
FIG. 2 is an explanatory cross sectional view of a structure in which a barrier membrane is held, by using an embodiment of a cover screw for a dental implant in accordance with the present invention, on the oral cavity side of an implant fixture implanted in an implantation hole formed in a mandible of a missing tooth portion.

Process 2: The screw 3a of the main body 3 is screwed into the threaded hole 1a which is open on the oral cavity side of the implant fixture 1, and the implant fixture 1 to which the main body 3 is fixed on the oral cavity side is implanted in the implantation hole (FIG. 3-2).

Process 3: The absorbable or non-absorbable barrier membrane 5 which is trimmed so as to have a desired size and has a penetration hole at the predetermined position in which the screw 4c of the membrane fixing screw 4 is to be inserted, is disposed so as to cover the exposed alveolar bone of the mandible and the bone defect portion if it exists. At the same time, the screw 4c of the membrane fixing screw 4 is screwed into the threaded hole 3c of the main body 3 fixed to the implant fixture 1 on the oral cavity side, resulting in holding the barrier membrane 5 between the face 3b of the main body 3 on the oral cavity side and the head 4a of the membrane fixing screw 4 (FIG. 3-3).

Process 4: The cut and opened gingival flap is returned to the original position to cover the exposed alveolar bone of the mandible with the gingival flap, and the gingival flap is sutured at the cut and opened site (FIG. 3-4).

The first operation is completed by the above mentioned four processes. Until the second operation, it takes 3–6 months, during the time the implant fixture 1 implanted in the implantation hole formed in the mandible of the missing tooth portion is connected to the mandible within the implantation hole.

Process 5: In case of the absorbable barrier membrane 5, in order to expose the cover screw 2 for a dental implant, either a gingiva portion corresponding to the cover screw 2 for a dental implant: is removed by a gingival punch, or the gingiva portion is cut and opened to make a gingival flap at the top of the alveolus in which the implant fixture 1 is implanted (FIG. 3-5).

Process 5': In case of the non-absorbable barrier membrane 5, in order to expose the cover screw 2 for a dental implant, a gingival flap is cut and opened to make a gingiva petal at the top of the alveolus in which the implant fixture 1 is implanted (FIG. 3-5').

Process 6: The membrane fixing screw 4, the main body 3 screwed in the implant fixture 1 and the tissue barrier 5 (if this is non-absorbable) are detached from the implant fixture 1. The healing abutment 6 is screwed into the threaded hole 1a of the implant fixture 1 which is open on the oral cavity side of the implant fixture 1. The healing abutment 6 includes an end portion on the implant fixture 1 side having the size same as that of the end portion of the implant fixture 1 on the oral cavity side, a length larger than the thickness of the surrounding gingiva, and a shape on the implant fixture 1 side identical to that of an abutment. In case that the gingiva was cut and opened to make the gingival flap, after the gingival flap is returned to the original position to expose the healing abutment 6 and to cover the exposed alveolar bone of the mandible with the gingival flap, the gingival flap is sutured at the cut and opened site (FIG. 3-6).

As a result, the second operation is completed.

The wound by the second operation is healed after about one month. After the gingiva touches the healing abutment 6 on the implant fixture 1 side, the healing abutment 6 is removed, and an abutment having a shape on the implant fixture 1 side identical to that of the healing abutment 6 on the implant fixture 1 side is disposed in the implant fixture 1 on the oral cavity side. The abutment is fixed to the implant fixture 1 on the oral cavity side by screwing an intermediate bolt penetrating the abutment in the threaded hole 1a of the implant fixture 1. A gold cylinder having a dental prosthesis on the outside is disposed on the abutment on the oral cavity side. The dental prosthesis is fixed to the implant fixture 1 on the oral cavity side via the abutment by the intermediate bolt penetrating the gold cylinder or by screwing the gold screw in the threaded hole formed in the abutment.

Thus, the operation of the dental implant is completed.

Instead of the method to use a bridge or a denture which has been generally employed as the dental prosthetic method in a missing tooth portion, the operation for a dental implant has been developed and carried out in order to solve the defects of the conventional method. In the cover screw for the dental implant in accordance with the present invention as mentioned above in detail, the barrier membrane, which provides a space for a regenerated bone under the periosteum by means of the guided tissue regeneration method using the barrier membrane while the implant fixture implanted in the implantation hole formed in the mandible of the missing tooth portion is connected to the mandible within the implantation hole, can be formed surely in an ideal condition.

In other words, the cover screw for a dental implant includes the main body, which has the male screw to be screwed into the threaded hole opening on the oral cavity side of the implant fixture and the threaded hole with the small diameter formed on the face of the oral cavity side opposite to the screw side in parallel to the screw, and the membrane fixing screw, which has the head to hold the barrier membrane between the above mentioned face of the oral cavity side of the main body and itself and is screwed into the above mentioned threaded hole with the small diameter of the main body. Therefore, when the guided tissue regeneration method is carried out, pins which are driven in the alveolar bone to fix the barrier membrane are not used, or even if it is used, the number of pins used can be reduced remarkably. As a result, not only the complexity of fixing the barrier membrane but also the invasion into the alveolar bone can be dissolved or reduced.

In addition, since the head of the membrane fixing screw to hold the barrier membrane exists on the face of the oral cavity side of the main body connected to the implant fixture, in the second operation wherein the cover screw is detached and the healing abutment is screwed in the threaded hole of the implant fixture in the condition that a bone grows and touches the face on the oral cavity side of the cover screw, an amount of the bone to be cut, if required, can be reduced to the minimum. Since a process which may cause the mechanical face property of the face of the implant fixture on the oral cavity side to become worse is not necessary, in the second operation, there will be no possibilities such that the healing abutment can not be fixed closely to the implant fixture and the abutment can not be fixed closely to the implant fixture when the healing abutment is detached and the dental prosthesis is fixed.

Even if there is a bone defect portion around the oral cavity side of the implant fixture in the alveolar bone of the mandible in which the implantation hole for the implant fixture is formed in the missing tooth portion, there is no possibility that a portion of the fixed barrier membrane on the implant fixture side sinks in the bone defect portion, and an undesirable periodontal tissue comes out from a boundary between the portion of the implant fixture on the oral cavity side and the hole of the barrier membrane. Such undesirable events may happen in the method such that the barrier membrane with the hole corresponding to the cover screw is disposed over the cover screw screwed into the implant fixture, and the barrier membrane is fixed to the mandible by driving absorbable or non-absorbable pins into the mandible.

The following undesirable events, which happen in the method in which the barrier membrane is fixed by disposing it between the implant fixture and the cover screw, when the cover screw is screwed into the implant fixture, does not happen:

1. In case of using a non-absorbable membrane as the barrier membrane, there is a possibility that the mechanical surface property of the face of the implant fixture on the oral cavity side becomes worse when the barrier membrane is attached or removed. Consequently, it may happen that during the second operation, the healing abutment can not be fixed closely to the implant fixture, or when the healing abutment is removed and the dental prosthesis is fixed, the abutment can not be fixed closely to the implant fixture.

2. In case of using the absorbable barrier membrane, as the barrier membrane is absorbed, an undesirable periodontal tissue may invade between the face of the implant fixture on the oral cavity side and the cover screw.

3. When the above mentioned invasion happens, there is a possibility that during the removal of the invaded tooth tissue, the mechanical face property of the face of the implant fixture on the oral cavity side becomes worse, resulting in that during the second operation, the healing abutment can not be fixed closely to the implant fixture.

4. When the healing abutment is removed and the dental prosthesis is fixed, the abutment can not be fixed closely to the implant fixture.

In addition, after the wound by the first operation is healed, the bone tissue grows enough to the oral cavity side of the implant fixture beyond the face of the implant fixture on the oral cavity side.

The cover screw for a dental implant in accordance with the present invention includes the main body with a shape approximately identical to that of the conventional cover screw, and the membrane fixing screw. The main body has the male screw to be screwed into the threaded hole opening on the oral cavity side of the implant fixture and the threaded hole with the small diameter which is formed on the face of the oral cavity side opposite to the screw side in parallel to the screw. The membrane fixing screw is screwed into the above mentioned threaded hole with the small diameter and has the head for holding the barrier membrane between the above mentioned face of the main body and the head. Therefore, the cover screw for the dental implant of the present invention can be produced according to the conventional manufacturing technique.

As described above, according to the present invention, the barrier membrane which is either absorbable or non-absorbable can be used. When a filling material such as self bone and bone graft material is filled in a space given by the barrier membrane, it becomes easy to maintain the space, and the filler can be held surely by covering the filled portion with the barrier membrane. In addition, the present invention has several advantages as described previously. Therefore, it will contribute to a dental field to a great extent.

While the invention has been explained with reference to the specific embodiment of the invention, the explanation is illustrative and the invention is limited only by the appended claims.

What is claimed is:

1. A cover screw for a dental implant to seal a threaded hole of an implant fixture formed in a mandible or a maxilla, comprising:

a main body including a first male screw to be screwed into the threaded hole of the implant fixture, an outer face formed on a side opposite to the male screw and facing an oral cavity, and a threaded hole formed on a side of the outer face and having a diameter smaller than that of the male screw and extending parallel to the male screw, and a membrane fixing screw having a head for holding a barrier membrane between the main body and the head, and a second male screw to be screwed in the threaded hole.

2. A cover screw for a dental implant as claimed in claim 1, wherein the implant fixture is implanted in an implantation hole formed in the mandible or maxilla of a missing tooth portion, said cover screw being attached to the implant fixture until the implant fixture is thoroughly connected to the mandible or maxilla in the implantation hole.

3. A cover screw for a dental implant as claimed in claim 1, wherein said threaded hole formed in the main body has a central axis coincident with that of the first male screw of the main body.

4. A cover screw for a dental implant as claimed in claim 1, wherein said main body and said membrane fixing screw are made of pure titanium or titanium alloy.

5. A cover screw for a dental implant as claimed in claim 1, wherein said outer face of the main body has a nonskid portion.

6. A cover screw for a dental implant as claimed in claim 1, wherein said membrane fixing screw has a connecting portion for a driver on the head thereof.

7. A cover screw for a dental implant as claimed in claim 1, wherein said main body has a head portion with the outer surface, an axis portion extending from the head portion on which the first male screw is formed, and a dent formed in the head portion around the axis portion.

8. A cover screw for a dental implant as claimed in claim 7, wherein said threaded hole extends through the head portion to the axis portion.

* * * * *